(12) United States Patent
Calavrezos et al.

(10) Patent No.: US 11,324,390 B2
(45) Date of Patent: May 10, 2022

(54) COUPLER FOR ENDOSCOPIC CAMERA

(71) Applicant: Promecon GmbH, Hamburg (DE)

(72) Inventors: Alexander Calavrezos, Hamburg (DE); Philipp Kraus, Munich (DE); Lenika Calavrezos, Munich (DE)

(73) Assignee: PROMECON GMBH, Hamburg (DE)

(*) Notice: Subject to any disclaimer, the term of this patent is extended or adjusted under 35 U.S.C. 154(b) by 593 days.

(21) Appl. No.: 16/208,137

(22) Filed: Dec. 3, 2018

(65) Prior Publication Data

US 2019/0167374 A1 Jun. 6, 2019

(30) Foreign Application Priority Data

Dec. 4, 2017 (EP) .................................... 17205136

(51) Int. Cl.
*A61B 1/00* (2006.01)
*A61B 1/05* (2006.01)
(Continued)

(52) U.S. Cl.
CPC ........ *A61B 1/00105* (2013.01); *A61B 1/0014* (2013.01); *A61B 1/00126* (2013.01);
(Continued)

(58) Field of Classification Search
CPC ............ A61B 1/00105; A61B 1/00126; A61B 1/00131; A61B 1/00195; A61B 1/042
See application file for complete search history.

(56) References Cited

U.S. PATENT DOCUMENTS

| 4,905,082 A | 2/1990 | Nishigaki et al. |
| 5,792,045 A | 8/1998 | Adair |

(Continued)

FOREIGN PATENT DOCUMENTS

| JP | H02285316 | 11/1990 |
| JP | H10165362 | 6/1998 |

OTHER PUBLICATIONS

Extended European Search Report dated Jun. 11, 2018, issued in related European Application No. 17205136.9.
(Continued)

*Primary Examiner* — Aaron B Fairchild
(74) *Attorney, Agent, or Firm* — Seager, Tufte & Wickhem, LLP

(57) ABSTRACT

The present disclosure relates to an endotherapy camera coupler. The coupler may detachably couple an endotherapy eyepiece cap to a camera and may support a drape for covering the camera. In one example, the coupler comprises an optically transmissible and liquid impermeable member configured to be arranged in an optical path between the eyepiece cap and the camera, a base holding the optically transmissible and liquid impermeable member in the optical path, a receiving portion for the eyepiece cap, wherein the receiving portion comprises a base-side receiving portion configured to receive the eyepiece cap along an insertion path extending in one direction, and a liquid barrier provided in the receiving portion and configured for hindering or preventing liquid from entering between the eyepiece cap and the optically transmissible and liquid impermeable member when the eyepiece cap is coupled to the camera. Other examples of devices and methods of use are described.

15 Claims, 11 Drawing Sheets

(51) Int. Cl.
*A61B 1/04* (2006.01)
*A61B 46/10* (2016.01)
*A61B 17/00* (2006.01)

(52) U.S. Cl.
CPC ...... *A61B 1/00131* (2013.01); *A61B 1/00142* (2013.01); *A61B 1/00195* (2013.01); *A61B 1/042* (2013.01); *A61B 1/053* (2013.01); *A61B 1/00128* (2013.01); *A61B 46/10* (2016.02); *A61B 2017/00477* (2013.01)

(56) References Cited

U.S. PATENT DOCUMENTS

| | | | |
|---|---|---|---|
| 5,810,620 A | | 9/1998 | Kobayashi et al. |
| 5,868,665 A | * | 2/1999 | Biggs ................ A61B 1/00128 600/112 |
| 2015/0112137 A1 | | 4/2015 | Hogrefe et al. |

OTHER PUBLICATIONS

Summons to attend oral proceedings purusant to Rule 115(1) EPC, for Application No. 17205136.9, dated Dec. 23, 2020, 26 pages.

\* cited by examiner

COUPLER FOR ENDOSCOPIC CAMERA

CROSS-REFERENCE TO RELATED APPLICATIONS

This application claims the benefit of priority under 35 U.S.C. § 119 to European Patent Application No. 17205136.9, filed Dec. 4, 2017, entitled "Coupler for Endoscopic Camera," which application is incorporated herein by reference in its entirety.

FIELD

The present disclosure relates to medical devices and particularly to couplers and methods of use for detachably coupling an endotherapy eyepiece cap to a camera and supporting a drape for covering the camera.

BACKGROUND

Modern surgical endoscopes can be connected to video cameras in order to generate and display an image. For this purpose, e.g., the international standard ISO/TS 18339:2015 (en) "Endotherapy devices—Eyepiece cap and light guide connector" specifies the design of the eyepiece cap and the light guide connector of an endoscope to enable the combination of products from different manufacturers. The eyepiece cap is the part of the endoscope located at the proximal end of the endoscope to which a photographic or video camera can be attached. As specified by said standard, the eyepiece has a generally conical shape with a lumen for optical image transmission. There may be similar specifications in other standards.

While the endoscope can be sterilized, a camera for use with the endoscope is usually not sterile. In order to maintain surgical sterility, the camera can be covered or enclosed by a sterile drape or the like.

One way of covering the camera is by attaching a drape, such as a tubular plastic film to the eyepiece cap and thereby enclosing the camera. This film may, for example, be firmly taped to the eyepiece cap, thus creating a sterile barrier. In many surgical procedures, however, the endoscope needs to be changed while the camera remains the same. When removing the tape, the sterile barrier may be broken.

Therefore, couplers may be used to maintain the sterile barrier when changing the endoscope. For example, a general configuration for a coupler is known that connects the eyepiece cap to the camera, creates a sterile barrier therebetween with the help of a drape, and allows transmission of the image. With such a coupler, the endoscope may be exchanged during an ongoing surgery while maintaining the sterile barrier.

Known couplers, however, may have multiple downsides. One challenge is the quality of optical transmission. Depending on the type of surgery, fluids and/or humidity may enter in the optical path between coupler and eyepiece of the endoscopic device with potential negative effects on the image quality. Especially in surgical applications that require inserting the endoscope from below, gravity may cause fluids to flow towards the coupler. Another challenge is creating a firm mechanical connection between endoscope and coupler and the connection of the drape. Further challenges are poor ergonomics, production complexity and the price of such a coupler, which is typically a disposable product.

SUMMARY

The present disclosure aims at overcoming or at least minimizing these challenges. In particular, it is an object of the present disclosure to provide a coupler that can be used for reliably creating a sterile operation theater and maintaining a clear vision by a camera used in combination with an endoscope.

The present disclosure relates to embodiments of an endotherapy camera coupler, and methods for their use, but the present disclosure is not limited to endotherapy and the couplers described here may be applied in all fields of endoscopy. In one embodiment, a coupler may detachably couple an endotherapy eyepiece cap to a camera and may support a drape for covering the camera. The coupler may comprise an optically transmissible and liquid impermeable member configured to be arranged in an optical path between the eyepiece cap and the camera. It may further comprise a base holding the optically transmissible and liquid impermeable member in the optical path. The coupler may comprise a receiving portion for the eyepiece cap, wherein the receiving portion may have a base-side receiving portion configured to receive the eyepiece cap along an insertion path extending exclusively in one direction. Also, the coupler may comprise a liquid barrier configured for hindering or preventing liquid from entering between the eyepiece cap and the optically transmissible and liquid impermeable member when the eyepiece cap is coupled to the camera. The liquid barrier may be provided in the receiving portion.

The camera may be attached to one side of the coupler, and the eyepiece cap may be attached to the other side of the coupler. The coupler may support a drape which is configured to cover the camera. The drape may also cover a cable that connects to a display unit, computer, or the like. The drape may be made from plastic material or any other suitable material that allows sterility and may, for example, be a film or fabric, or the like. This helps in creating a sterile barrier between the endoscope and a non-sterile camera.

The coupler may be detachably coupled to an endotherapy eyepiece cap. Thus, the endoscope can be interchanged during surgery while the sterile barrier is upheld.

The coupler may comprise an optically transmissible and liquid impermeable member that may be configured to be arranged in an optical path between the eyepiece cap and the camera. This member may allow the light coming from the endoscope lens to be optically transmitted from one side of the coupler to the other side. When the coupler is properly placed between endotherapy eyepiece cap and the camera, the optically transmissible and liquid impermeable member may be in the optical path.

The member may be made from glass or plastic materials, and may optionally have optical characteristics (e.g., a lens, a filter or the like). The member may be transmissible for all, close to all or just some light. For example, only light of particular wavelengths may be transmitted, while light of other wavelengths may not be transmitted.

The member may also be liquid impermeable so that liquids, including water, water solutions such as blood, and medical liquids cannot pass through the member during surgical procedures (i.e., at normal temperatures, pressures and/or times under which surgical procedures are performed). When the member is placed in the optical path between the eyepiece cap and the camera, liquids may be hindered or stopped from passing towards the optical path and particularly from the side of the eyepiece cap to the side of the camera. The member may be made from one or more materials, such as glass, plastics, organic or non-organic crystals. It may be cut and/or polished.

The member may be a distinct component of the coupler or an integral part of a coupler component. For example, the member and the base may be an integral component.

The member may fulfill multiple functions. For example, it may comprise a connector end that allows connecting the camera. Also, it may be configured to support the drape.

The coupler may comprise a base configured to hold the optically transmissible and liquid impermeable member in the optical path. The base and the member may be two or more components, or they may be one integral component. The base may form a platform for supporting further functions or components of the coupler or associated parts. The base may circumferentially surround the member.

The coupler may comprise a receiving portion for the eyepiece cap, wherein the receiving portion may comprise a base-side receiving portion configured to receive the eyepiece cap, including along an insertion path extending exclusively in one direction. In other words, the eyepiece cap may be inserted in the receiving portion along a unidirectional insertion path, for example, in an axial direction without any movement in another direction being required.

The receiving portion may be formed in a portion of the base, thus forming a base-side receiving portion, and a portion of a fastener, thus forming a fastener-side receiving portion.

The base-side receiving portion may be configured to receive the eyepiece cap along an insertion path extending exclusively in one direction. When the eyepiece cap is moved towards the coupler and brought into contact with the coupler, it may be received by the receiving portion and at least partly physically contact the receiving portion. An insertion path may be the sum of positions of the eyepiece cap relative to the coupler when it approximates and makes contact with the coupler. The receiving portion may have a plurality of different insertion paths. However, in some embodiments, at least one of the insertion paths extends exclusively in one (straight) linear direction. This direction may be generally parallel to the optical path close to the receiving portion and/or perpendicular to an end surface of the eyepiece cap.

The base-side receiving portion may generally resemble a depression, well or recess within the base, receiving the eyepiece cap therein.

The coupler may furthermore comprise a liquid barrier provided in the receiving portion and configured to hinder or prevent liquid from entering between the eyepiece cap and the optically transmissible and liquid impermeable member when the eyepiece cap is coupled to the camera. Such liquid barrier may comprise geometric features which, when the eyepiece cap is coupled to the camera, hinder or prevent liquid from entering between the eyepiece cap and said member. The liquid barrier may be partly or fully in contact with the eyepiece cap to thereby perform its function. Additionally or alternatively, the liquid barrier may be spaced from the eyepiece cap in the coupled state. The liquid barrier may comprise one or more of various physical mechanisms to hinder or prevent liquid from passing, for example, gravity, fluid mechanics, solid material/diffusion block. The risk of ingress of liquid between the eyepiece cap and the member may be generally present from multiple directions. In some embodiments, the liquid barrier covers all such directions. This may depend on the direction of gravity and/or application. When no liquid enters between the eyepiece cap and said member, the optical path may not be influenced by liquid. This may improve or may at least maintain the quality of optical transmission. The absence of liquid may also prevent the emergence of fog, which could also compromise light transmission.

A base-side receiving portion configured to receive the eyepiece cap along an insertion path extending exclusively in one direction may comprise a defined insertion path. An insertion path extending in exclusively one direction may allow a defined design of the receiving portion and its liquid barrier. The defined insertion path may improve the function of the liquid barrier to hinder and prevent liquid from entering when coupled. Furthermore, the insertion path may contribute to the strength and reliability of a mechanical connection between coupler and eyepiece cap. An insertion path extending exclusively in one direction may have the advantage of a more defined positioning of the eyepiece cap in the base-side receiving portion.

The optically transmissible and liquid impermeable member may be an integral part of the base. For that purpose, the member and the base may be one solid component. They may be of one single material, in which case this material may have to allow the member to be optically transmissible and liquid impermeable at least in the area of the optical path. The integral part may also be of multiple materials and/or components, for example, in the case of multi component injection molded or insert molded configurations.

The base may have an opening for attachment of the optically transmissible and liquid impermeable member in the optical path. In this case, the member and the base may be of at least two parts, and the base may have an opening for attachment of the member. For example, the member may be of an optically transmissible and liquid impermeable material, and the base may be of a second different material. The opening may surround the optical pathway, including circumferentially. The opening may be round, including generally circular. It may have a closed (e.g., "lake") design or an open (e.g., "bay") design. The attachment of the member may be made in several ways, for example, by interference fit, adhesion, clamping, etc.

The optically transmissible and liquid impermeable member and the base may be connected to form a liquid-tight seal, for example, using a bayonet-type mount such as a snap-fit bayonet mount. Depending on the design of the member and the base, a liquid-tight seal may have the advantage that no liquid can enter between the member and the base, thereby contributing to the sterile barrier. A bayonet mount may be suitable, for example, with the opening being generally round and a rotational relative movement may be possible for attachment. A bayonet mount may include a male connector and a corresponding female connector that cooperate for a locking attachment. A snap-fit bayonet mount may use a snap-fit mechanism, e.g., a cantilever snap-fit mechanism or an annular snap fit mechanism, to lock the bayonet mount in an engaged configuration. A cantilever of a bayonet mount snap-fit mechanism may be positioned on either the inner or the outer bayonet mount part. An elastic movement of a snap-fit lever may be used in one or more of several directions, for example, in an axial or in a radially inward or radially outward direction. It may be a permanent or non-permanent snap-fit with one or multiple snap-fit levers.

The liquid barrier may circumferentially surround the area of the optical path, i.e., the area of the base having the opening holding the member. Depending on the use of the coupler and its orientation relative to the direction of gravity, the liquid barrier may hinder or prevent liquid from entering between the eyepiece cap and the member from multiple directions. If, for example, the eyepiece cap has the generally round geometry described in the international standard ISO/TS 18339:2015, then the liquid barrier may generally correspond to the round geometry, thereby hindering or preventing liquid from entering from all or some radial directions. The liquid barrier may be generally round from a top view.

According to one embodiment of the present disclosure, the liquid barrier may comprise a sealing surface configured for contact with an opposing sealing surface of the eyepiece cap, thereby creating a seal therebetween. This liquid barrier may have the advantage of reliably hindering or preventing liquids from entering between the member and the base, under a wide range of conditions in terms of orientations, temperatures and pressures. Furthermore, the seal may not rely on gravity. The sealing surfaces may be opposing planar surfaces or opposing cylindrical surfaces or opposing conical surfaces or any combination thereof. Endotherapy eyepiece caps may have a variety of designs. They may also vary within compliance with international standard ISO/TS 18339:2015. Such standard compliant eyepiece caps may have multiple surfaces suited for creating a seal with an opposing surface, including a planar surface, a cylindrical surface, a conical surface and combinations thereof. The sealing surface of the liquid barrier may be configured to create a seal with many geometric variations of eyepiece caps.

The sealing surface of the liquid barrier may be of a base-side receiving portion or a fastener-side receiving portion or other portions or a combination thereof. For example, the sealing surface may be a planar surface of a base-side receiving portion. Or, in another example, the sealing surface may be a cylindrical surface on one or more fastener-side receiving portions.

The liquid barrier may comprise a sealing element, including a sealing ring, and the sealing surface may be formed by a surface of the sealing element. The sealing ring may be an O-ring, but other cross-sectional shapes of the sealing ring such as oval, square, rectangular, or other polygonal shapes are also possible. The sealing element may be formed from an elastic and/or malleable material and/or a material that adapts to the opposing sealing surface to form the seal. The sealing element may be compatible to a range of pressures of the opposing surfaces. The sealing element may be of a liquid impermeable material. The sealing surface of the sealing element may create one seal with the opposing sealing surface of the eyepiece cap and it may create another seal with another part, for example the base. The receiving portion may in this case include a sealing element because the liquid barrier comprises a sealing element. The sealing element may be interchangeable. The sealing element may be held by the base, for example, using one or more radially inwardly extending protrusions, one or more slots, one or more circumferential protrusions, one or more undercuts and/or a press fit. The sealing element may be an integral part of the base. For example, the sealing element may be made from the same material as the base and may be formed as a thin (flexible) web of said material. Alternatively or additionally, the sealing element may be formed to the base by multi-component injection molding process, or the like.

According to one embodiment of the present disclosure, the liquid barrier may comprise a dam radially outside of the optical path and a liquid collection portion radially outside of the dam. A dam may be a geometric design feature that may prevent or hinder liquids from passing under certain conditions. A liquid collection portion may include geometric features that allow permanent or non-permanent storage, guidance and/or drainage of liquids. A dam may make use of gravitational and/or fluid mechanical and/or microfluid mechanical effects to prevent or hinder liquids from passing. This may depend on the properties of liquids, depending on the type of liquid, e.g., water, blood, water solutions, saline solutions, etc. The dam may include a step or an elevation, in combination with which a fluid will not pass. The dam may include a maze or labyrinth to prevent or hinder liquids from passing. The functioning of the dam may depend on the amount of liquid, the liquid collection portion and liquid pressure. The liquid collection portion may be radially outside of the dam, for example, so as to avoid allowing liquid to advance radially inward of the dam towards the area of the optical path.

The liquid collection portion may comprise one or more recesses arranged at least partially around the circumference of the dam. The geometric design of one or more recesses may guide and/or collect liquid. The liquid collection portion may use gravitational and/or fluid mechanical and/or microfluid mechanical effects.

The coupler may comprise one or more draining channels for discharging liquid from the barrier. For example, the one or more draining channels may discharge liquid from a region close to a sealing element and/or from a region close to a liquid collection portion and/or a dam. The one or more draining channels may contribute to the function of the liquid barrier by discharging liquid and preventing a collection or accumulation of liquid.

The coupler may comprise at least one fastener for fastening the eyepiece cap to the coupler. The connection may be done in a reversible manner and is therefore detachable or releasable. The at least one fastener may rely on the geometry of the eyepiece cap in order to apply forces. It may fasten using a force in one or more directions, for example in a direction generally parallel to the optical path or for example in a direction generally transverse to the optical path, or both. The at least one fastener may be part of the base, or separate part(s). The fastening of the eyepiece cap to the coupler may consider the design of the base-side receiving portion and the liquid barrier. For example, if the liquid barrier comprises a sealing element which requires a certain surface pressure for its sealing effect, the fastener may be configured to support such a pressure or provide respective forces.

The fastener may be movably mounted to the base and may be configured to be moved from and to an open state and a closed state. In an open state, the eyepiece cap may not be fastened to the coupler and may be removed from the coupler. In a closed state, the eyepiece cap may be fastened to the coupler. In the open state, the eyepiece cap may be received along an insertion path extending exclusively in one direction, i.e., along a unidirectional path. For example, the at least one fastener may be moved in a generally straight direction generally transverse to the optical path away from the optical path towards an open state. In this example, the insertion path may extend exclusively in a direction generally parallel to the optical path. In another example, the at least one fastener may be moved in a generally circumferential direction, for example, around a point in the optical path. The relative movement between fastener and base may be linear, or rotational or a multiple degree movement or a combination thereof. The fastener may be detachably mounted to the base. Multiple fasteners may move in a generally symmetrical way. For example, in case of two fasteners, they may be moved in opposite directions.

The fastener may comprise a fastener-side receiving portion, wherein the receiving portion may be cooperatively formed by the base-side receiving portion and the fastener-side receiving portion. A fastener-side receiving portion may be a portion of the at least one fastener which is configured to at least partially physically contact the eyepiece cap. The fastener-side receiving portion may comprise the liquid barrier or parts thereof. It may comprise a sealing element of the liquid barrier. It may also comprise a dam or other types of liquid barriers. The fastener-side receiving portion may be cooperatively formed by some or all of the fasteners.

The fastener may be slidable or pivotable or both relative to the base to hold the eyepiece cap in place in the closed state, and to release the eyepiece cap in the open state. The eyepiece cap may be in place in the closed state when it is received by the receiving portion and the optically transmissible and liquid impermeable member is arranged in an optical path between the eyepiece cap and the camera.

The fastener may be configured to apply a compressive force in an axial and/or radial direction with respect to the eyepiece cap in the closed state, for example, so as to urge the eyepiece cap into the receiving portion, particularly the base-side receiving portion. Depending on the configuration of the liquid barrier, a certain range of compressive forces may be realized. A sealing element, for example, may make use of a compressive force. Also, a liquid barrier dam may make use of a force and/or defined positioning of the eyepiece cap. A compressive force may contribute to the firm mechanical connection and reliable positioning of the coupler. This may support image quality, endoscope handling and other benefits of a good coupler.

An axial direction with respect to the eyepiece cap may be generally parallel to an optical path and a radial direction with respect to the eyepiece cap may be generally orthogonal to an optical path. A compressive force between eyepiece cap and receiving portion may lead to a compressive pressure on contact surfaces therebetween.

Furthermore, the coupler may damp movements, especially vibrations, and thereby may improve image transmission quality, e.g., a soft and/or compressible sealing element may damp vibrations.

The fastener may engage contact portions on both sides of the base in an axial direction with respect to the eyepiece cap. If the fastener applies forces between the eyepiece cap and the receiving portion, the flux of force may determine the mechanical quality of the connection. For example, the fastener may be in contact with a contact portion on the eyepiece cap on one side of the base and on another side of the base. In an example, the eyepiece cap is one side of the base and the base-side receiving portion is generally located on the other (opposite) side of the base. Because the fastener may engage the contact portion on the eyepiece cap on the one side of the base and the contact portion on the other side of the base, the fastener may represent a roughly circular flux or distribution of forces, contributing to a reliable mechanical connection. The fastener may be in contact with a multitude of points, and thereby may contribute to a distributed flux of forces and/or a homogenous pressure.

The fastener and base may form a snap-fit mechanism, wherein, in the closed state, the fastener and base may be releasably snapped together, while the fastener may be biased towards the open state. The snap-fit mechanism may be a non-permanent cantilever snap-fit mechanism and optionally one or more levers of the cantilever snap-fit mechanism may be integral parts of the base. For example, the one or more fasteners may have one or more cantilevers each, corresponding to one or more grooves or recesses each in the base. In another example, the cantilevers are part of the base and the fastener has corresponding grooves or recesses. The snap-fit mechanism may be configured to transmit forces necessary for fastening. In the closed state, a bias of the fastener towards the open state may provide forces, e.g., so as to urge the eyepiece cap into the receiving portion. A bias may be realized by an elastic compression of the one or more fasteners and/or an elastic deformation of the base. A snap-fit mechanism may be easy to handle while providing a reliable fastener with force transmission and may be suited for surgical use. The fasteners may be multiple fasteners and may be configured to be arranged in a symmetrical way and/or configured to symmetrically provide forces. The fastener may have mechanically separate functions of fastening the eyepiece cap, guiding the movement of the fastener, snap-fitting of the fastener, and the like.

The receiving portion may comprise one or more radially inwardly extending projections that may be configured to position the eyepiece cap and/or a sealing element in the receiving portion. If, for example, the liquid barrier comprises a sealing element and this sealing element is a sealing ring (such as an o-ring), the sealing ring may be held in place by one or more radially inwardly extending projections, which may be positioned generally circumferentially around the sealing element. In this example, the projections may also position and/or guide the eyepiece cap, including along its insertion path. This may facilitate use and operation of the coupler and it may improve the mechanical connection.

The drape may be attached to the base, the optically transmissible and liquid impermeable member or both. The drape may be supported at the opening and/or between the member and the base. For example, a drape may be clamped or squeezed in between these parts or adhesively connected to one or both parts.

In embodiments of the disclosure comprising a dam, the insertion path may not be limited to having an insertion path extending exclusively in one direction. In other words, in any embodiment with a dam, the insertion path may not be limited.

The above summary of the disclosure is not intended to describe each embodiment or every implementation of the disclosure. Advantages and attainments, together with a more complete understanding of the disclosure, will become apparent and appreciated by referring to the following detailed description and claims taken in conjunction with the accompanying drawings.

BRIEF DESCRIPTION OF THE DRAWINGS

The disclosure will be further explained by referring to the figures. It is noted that the figures serve to explain certain features that may be optional to the disclosure.

The figures are not to be interpreted in a limiting way and any of the features discussed by referring to the figures may occur, alone or in combination with one or more other features, in other embodiments.

DETAILED DESCRIPTION

Figure 1A:
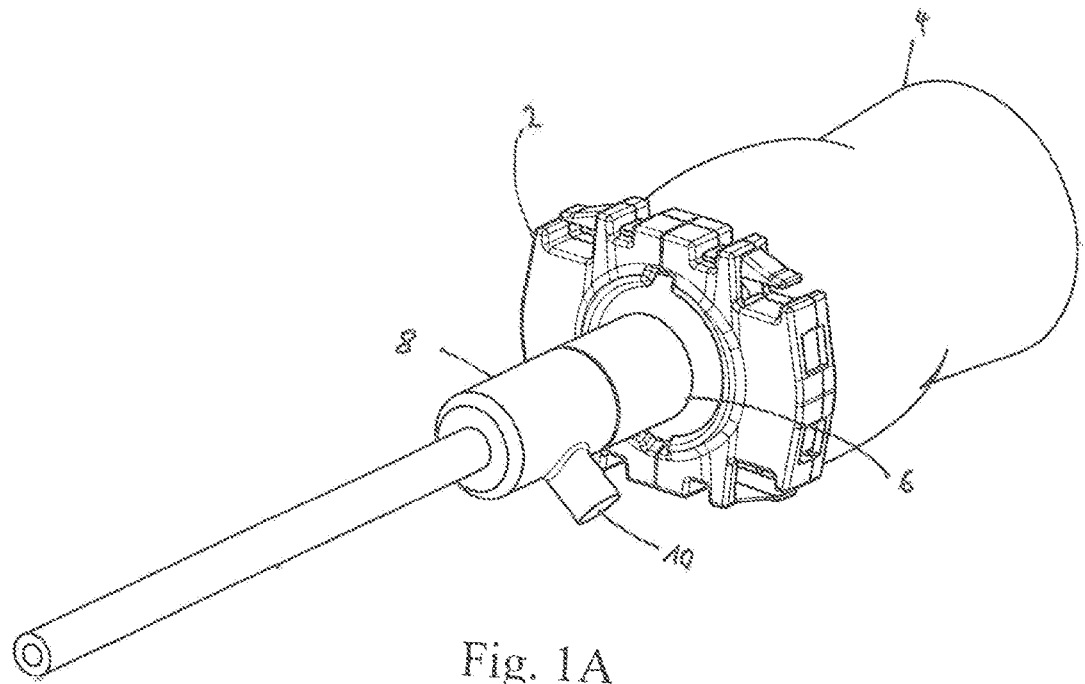
FIG. 1A shows a coupler according to an embodiment of the disclosure in the context of a drape and an endoscope with an eyepiece cap in a closed state.

For defined terms herein, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended to be only exemplary. Selected features of any illustrative embodiments may be incorporated into any other described embodiments unless clearly stated to the contrary.

The Figures schematically show embodiments of couplers 2 according to the disclosure with a drape 4 and an eyepiece cap 6. A base 12 may hold an optically transmissible and liquid impermeable member 14 in a generally central position, generally aligned with the eyepiece cap 6. Thus, the member 14 is arranged in an optical path 24 between the endoscope, eyepiece cap 6 and the camera. The member 14 has a camera connector portion 58 for connecting to a camera. The camera connector portion 58 may have a shape generally corresponding to the shape of the eyepiece cap 6. Hence, cameras designed to be attached directly to an eyepiece cap of an endoscope may be suited to be connected to the member, too. The member 14 may be of a solid, optically transmissible and liquid impermeable material. The optical path 24 transverses a part of member 14. The drape 4 may be supported by the base 12. It may be attached to the base 12.

Figure 1B:
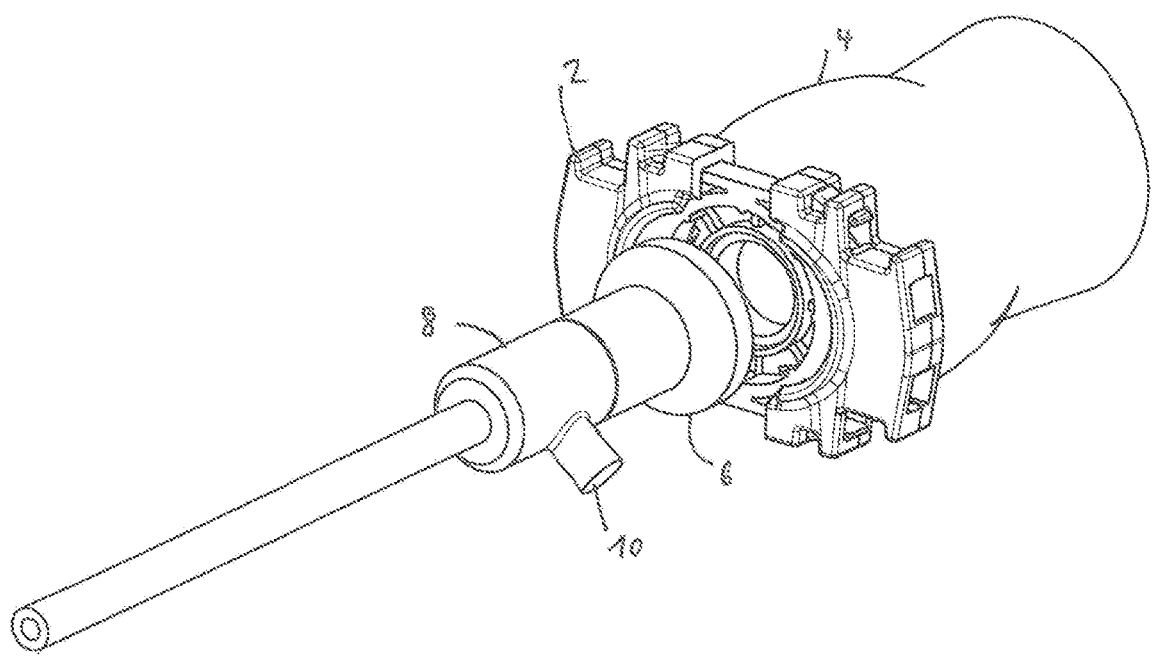
FIG. 1B shows the coupler of FIG. 1A in an open state.

FIGS. 1A and 1B show a coupler 2 of an embodiment of the disclosure in combination with a drape 4 and a part of an endoscope 8 with an eyepiece cap 6 and a light delivery system 10 in a perspective view. The drape 4 is only indicated schematically. Typically, the drape would extend further away from the endoscope so as to cover the camera in a medically required way. In FIG. 1B, the eyepiece cap is not shown coupled to the camera, but positioned at a distance relative to the coupler 2. The coupler 2 is shown in its open state so that the eyepiece cap 6 can be inserted into a receiving portion 16 of the coupler 2. FIGS. 1A and 1B do not show a camera, which may be positioned inside the drape and coupled to the coupler.

Figure 2:
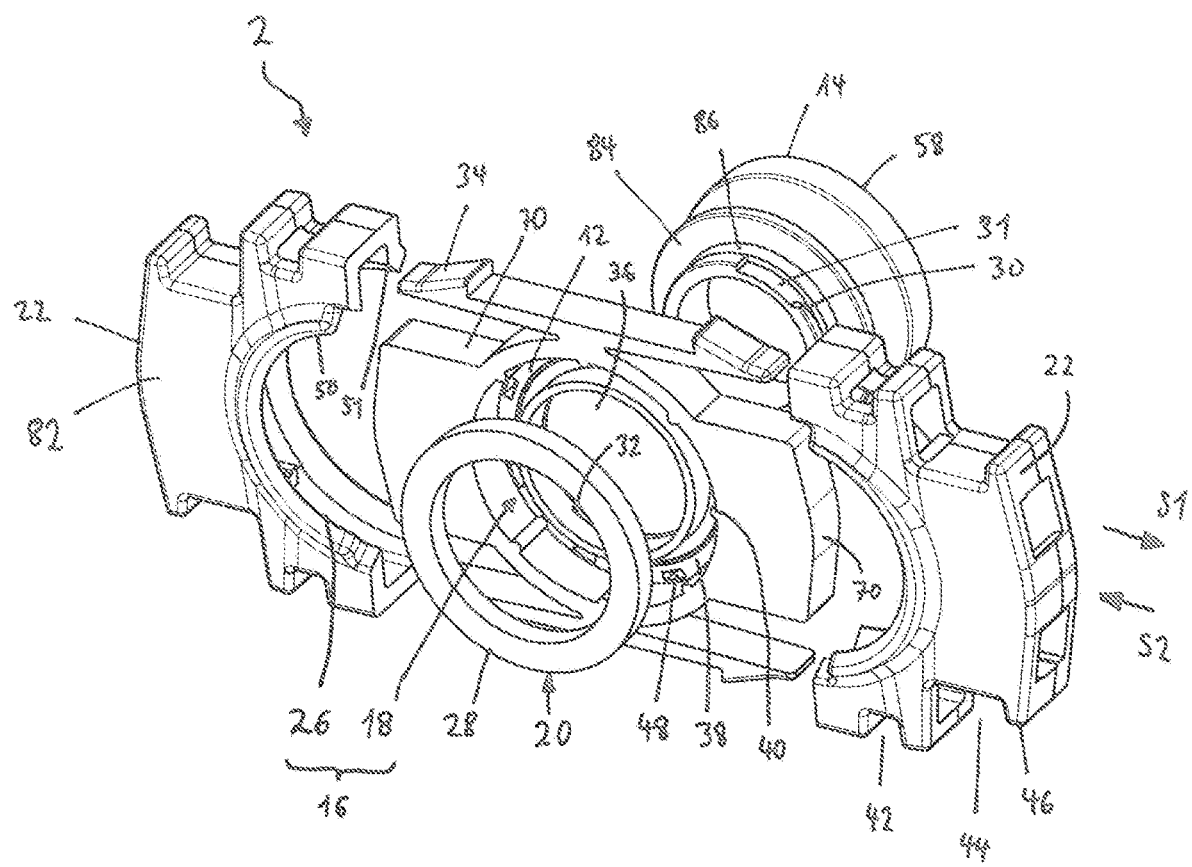
FIG. 2 shows an embodiment of a coupler according to an embodiment of the disclosure in an exploded view.

FIG. 2 shows an embodiment of the coupler according to the disclosure in an exploded view. The coupler may comprise base 12, two fasteners 22, optically transmissible and liquid impermeable member 14, receiving portion 16 for the eyepiece cap and liquid barrier 20 comprising sealing element 28. The optically transmissible and liquid impermeable member 14 may be held by the base in opening 36 and connected with the base 12 via a bayonet mount, wherein bayonet mount protrusions 32 are configured to engage with bayonet mount entry portions 31 and to rotate within the bayonet mount slot 30. Member 14 may comprise an axial abutment surface 84 and/or a radial abutment surface 86. When member 14 is connected to the coupler using the bayonet mechanism, the abutment surfaces may contact counter-surfaces on the side of the base 12. Thereby, a sealing effect between member 14 and base 12 may be achieved. The receiving portion 16 is preferably formed in a portion of the base 12, thus forming a base-side receiving portion 18, and a portion of the fasteners 22, thus forming a fastener-side receiving portion 26.

Figure 3B:
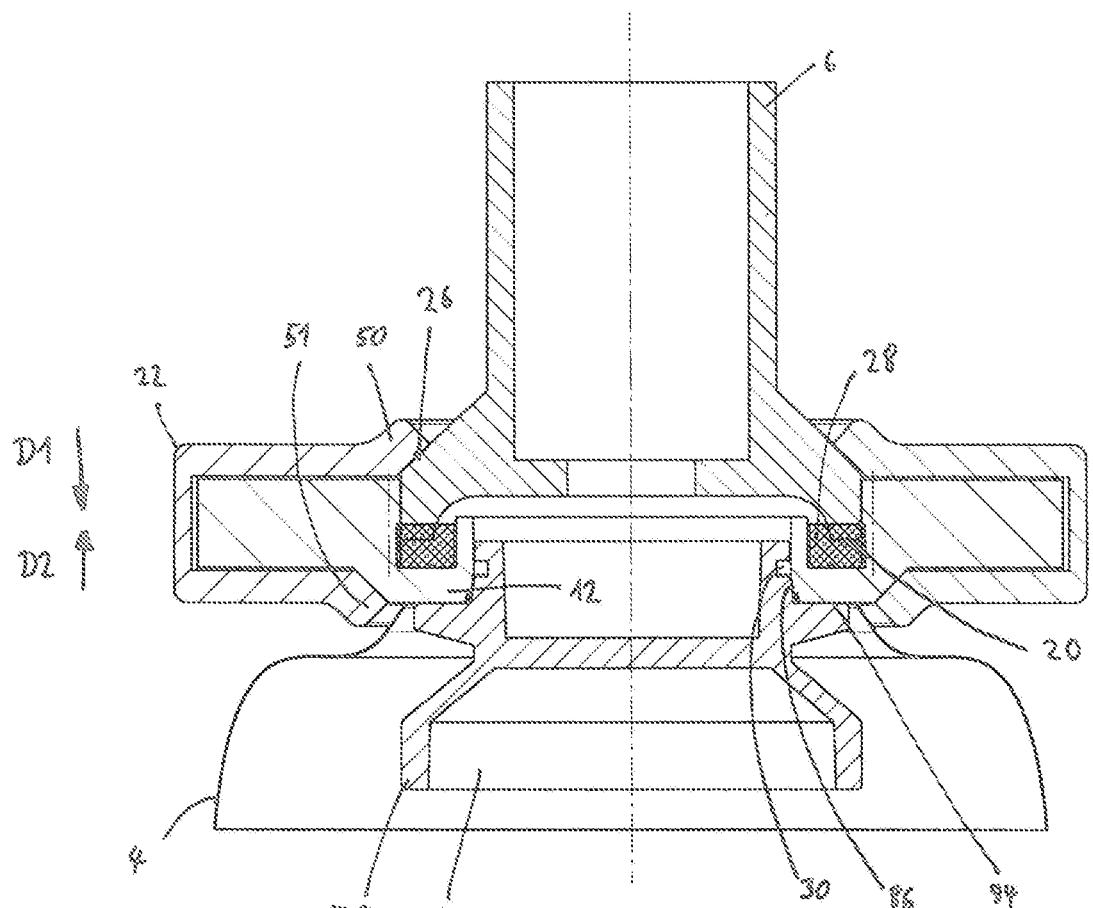
FIG. 3B shows a cross section through line A-A of FIG. 3A.

The fasteners 22 may be movable, e.g., slidable, in directions S1 and S2. A closed state of the coupler may be described as when both fasteners are in a position closer to the center of the base and fastening an eyepiece cap as also shown in FIG. 3B. Fasteners 22 may be configured to receive snap fingers 34. As can be seen in, e.g., FIG. 2 and FIG. 5, the fasteners 22 may have a first groove 42 and a second groove 44 for each snap finger 34. When the fastener is slid fully into the closed state and the snap-fit mechanism is closed, the hook 62 of snap finger 34 is in the second groove 44. Slope 64 enables deflection of the snap finger 34 in direction E1 by pushing the fastener 22, in direction S2 or respectively S1, against base 12. The snap-fit mechanism may be released by pressing the hook 62 or pressing on tab 66, thereby elastically bending the lever 60 and retracting the fastener 22 from the base 12. In a position between the second groove 44 and the first groove 42, the lever 60 may be biased towards the outside of the fastener. When the fastener is retracted further, the snap finger 34 may enter the first groove 42 and engage, thereby preventing a full retraction of the fastener and preventing a loss of individual parts within the surgical environment. This secures the fastener 22 in the open state. The first groove 42 may be too small for entry of average adult sized fingers, thereby preventing further retraction of the fastener. The fastener 22 may comprise a handle portion 82 for comfortable and practical use. End tips 46 may help holding fastener 22 when opening the fastening mechanism.

The fasteners 22 may also be configured to slide relative to the base 12. As can also be seen in FIG. 2 and FIG. 5, blocks 70 may comprise lateral block surfaces 72, block end surface 74, top block surfaces 76 and bottom block surfaces 80, which may guide the relative movement of the fasteners 22 and base 12 in direction S1 and S2. Fasteners 22 may have an internal geometry corresponding to the surfaces.

The base 12 may comprise a depression 38, the depression 38 being configured to accommodate multiple features. A base-side receiving portion 18 may be at least partly within the depression. The base-side receiving portion 18 may also be partly defined by the sealing element 28. The depression 38 may be configured to accommodate the sealing element 28. The sealing element 28 may be held in position, even when the eyepiece cap is not connected, e.g., by a press-fit with the base or by radially inwardly extending projections 40. The base may furthermore comprise draining channels 48.

Figure 4B:
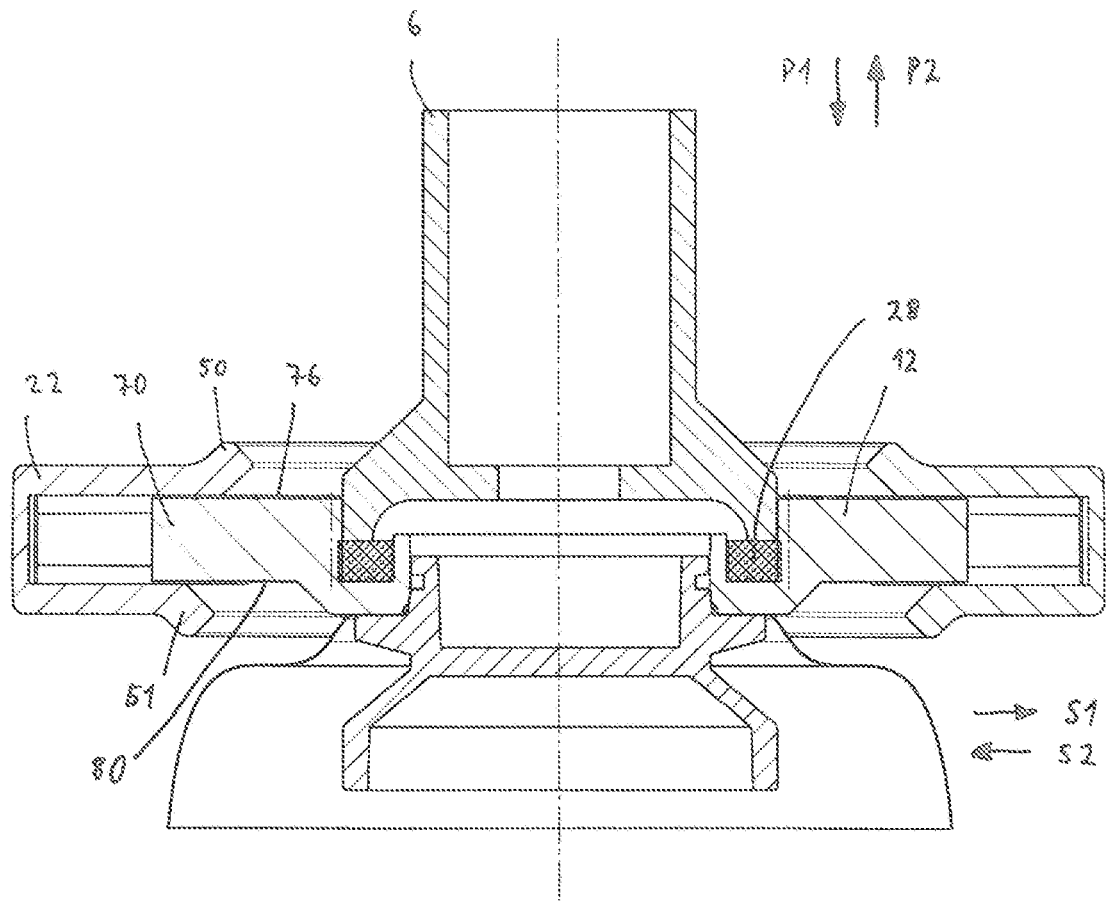
FIG. 4B shows a cross section through line A-A of FIG. 4A.

The base-side receiving portion 18 may be configured to receive the eyepiece cap 6 along an insertion path extending exclusively in one direction. The depression 38 formed in base 12 allows for the insertion of the eyepiece cap 6 along the direction of the axis of the eyepiece cap 6, which may correspond to the direction D1 shown in FIG. 3B. No undercuts or the like may be in the way in an open state when the eyepiece cap 6 is inserted. FIG. 4B, which shows the coupler in a cross-section in an open state with the fasteners 22 slid away from the center of the base in directions S1, respectively S2, also shows that the eyepiece cap 6 may be inserted in direction P1 with no obstacles in the way. In contrast, in the closed state shown in FIG. 3B, the upper semi-circular contact portions 50 close and are then positioned partly above the eyepiece cap 6 in the closed state.

Figure 3A:
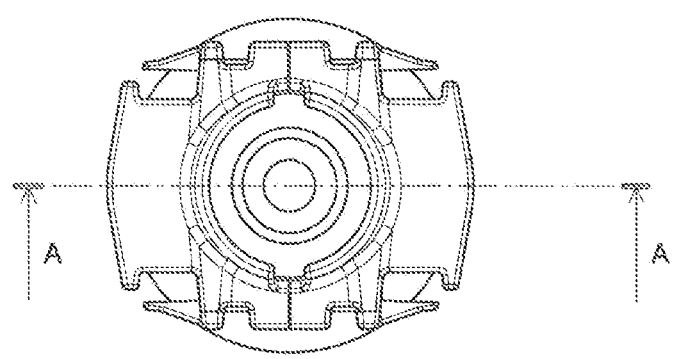
FIG. 3A shows the coupler of FIG. 2 in a closed state with a drape and an eyepiece cap in a top view.

FIG. 3A shows the coupler of FIG. 2 in a closed state with a drape 4 and an eyepiece cap 6. FIG. 3B shows a cross section through line A-A of FIG. 3A. In this embodiment, the liquid barrier comprises a sealing element 28, shown in the closed state of the coupler, wherein the sealing element 28 is slightly compressed at the interface with the circumferential end surface of the eyepiece cap. The sealing element 28 may be a sealing ring, e.g., an o-ring. It may be held by the base 12 and may create a seal together with a surface of the eyepiece cap 6. The sealing element 28 may be held in position, even when the eyepiece cap is not connected, e.g., by a press-fit with the base or, e.g., by radially inwardly extending projections 40. The fasteners 22 may hold the eyepiece cap in place in the closed state, as illustrated. The fasteners may be configured to apply a compressive force in an axial and/or in a radial direction with respect to the eyepiece cap in the closed state so as to urge the eyepiece cap into the receiving portion. Thereby, the sealing element 28 may be compressed and the sealing effect improved. For example, an upper semi-circular contact portion 50 of the fastener may engage the eyepiece cap and apply a force in the direction D1. Conversely, an opposite semi-circular contact portion 51 of the fastener may engage the lower side of the base 12 and apply a force in the direction D2. The sealing element 28 may be malleable and/or elastic and is arranged between the eyepiece cap 6 and the base 12. The upper semi-circular contact portion 50 of the fastener 22 may have a slope or be inclined in such a way that the movement of the fastener in direction of the eyepiece cap S2, which may also have an inclination in a cross-section view as seen in FIG. 3B, achieves a bias and a translation of bias force direction from the direction S2 into the direction of D1, respectively D2. With symmetric fasteners biased in the opposing directions of S1 and S2, the eyepiece cap may be advantageously biased into the sealing element 28. A semi-circular contact portion 50 may be beneficial for a homogenous force application and flux, reliable mechanics and an enhanced sealing effect.

FIG. 3B also shows axial abutment surface 84 and radial abutment surface 86 of member 14. When in contact with the base 12, a sealing effect may be achieved. Drape 4 may be attached to either of the two, and/or clamped and/or interlocked and/or adhesively connected in between.

In this embodiment, the receiving portion 16 may be formed in a portion of the base 12 and/or a portion of the fastener 22 and/or a portion of the sealing element.

Figure 4A:
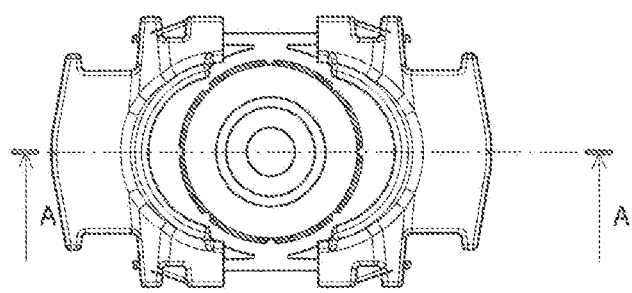
FIG. 4A shows the coupler of FIG. 2 in an open state with drape and eyepiece cap in a top view.

FIG. 4A shows the coupler 2 of FIG. 3A and FIG. 3B in an open state with drape 4 and eyepiece cap 6. FIG. 4B is a cross section through line A-A of FIG. 4A. The two fasteners 22 may be slid apart in a linear direction generally orthogonal to an axis of the eyepiece cap 6, e.g., one of the symmetric fasteners in direction S1 and the other in direction S2. FIG. 4B shows the sealing element 28 in an uncompressed or expanded state, with the eyepiece cap 6 slightly moved away (in direction P2) from its position seen in FIG. 3B. In the open configuration shown in FIG. 4B, the fasteners 22 are slid apart so as to release the eyepiece cap. This allows removal or separation of the eyepiece cap from the coupler.

Figure 5:
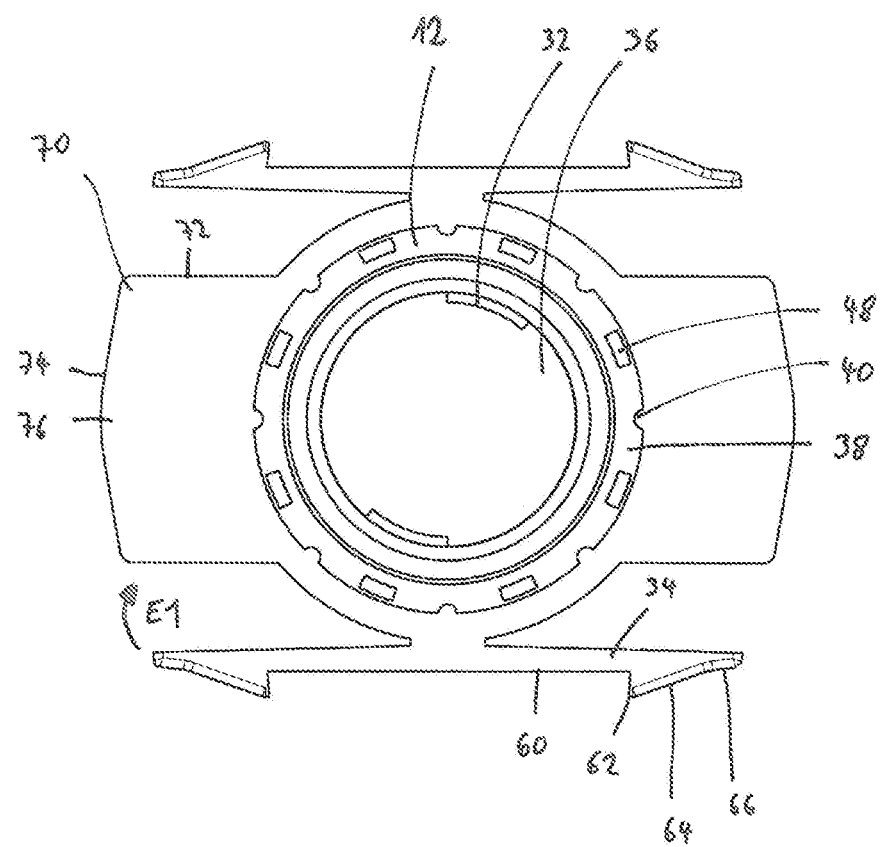
FIG. 5 shows a part of the coupler of FIG. 2 in a top view.

FIG. 5 shows a part of coupler 2 in a top view. Multiple functions are integrated into one part. Base 12 has an opening 36 for receiving member 14. The fasteners 22 may be slidable relative to the base. The two fasteners 22 and the base 12 may form two snap-fit mechanisms, wherein, in the closed state, the fasteners 22 and base 12 may be releasably snapped together, and the fasteners 22 may be biased towards the open state. The snap-fit mechanisms may be non-permanent cantilever snap-fit mechanisms and two levers of each snap-fit mechanism may be integral parts of the base 12. The four snap fingers 34 may represent the two levers of each snap-fit mechanisms as part of the base 12. The snap fingers 34 may have, among others, a hook 62 with an optional undercut for snapping into a closed state, a lever arm 60 for elastic movement, a slope 64 for interaction with the counterpart when entering the counterpart and a tab 66 as an interface for touching for releasing the snap-fit. The two snap-fingers 34 of one fastener 22 may be operated with two fingers, e.g., a thumb and an index finger. As shown above with reference to FIG. 2, the hook 62 may interact with first snap-fit groove 42 and second snap-fit groove 44. The latter may be large enough for interaction with tab 66 as interface, wherein the first snap-fit groove 42 may be too small for human fingers to enter, thereby preventing the fastener to be fully released and separated from the base 12.

The bayonet mount protrusions 32 may correspond to the bayonet mount slot 30. Reference is made to the above explanations on bayonet mounts.

The radially inwardly extending projections 40 may be configured to position the eyepiece cap 6 and/or a sealing element 28 in the receiving portion. A depression 38 may be configured to receive sealing element 28.

As seen in FIG. 2 and FIG. 5, the coupler 2 may comprise draining channels 48 for discharging liquid from the liquid barrier. For example, when the coupler is positioned in a way that the direction of gravity generally corresponds to direction D1, gravity will achieve the effect of liquid flowing through the draining channels 48 from the depression towards the other side of the base 12, thereby transporting the liquid away from the receiving portion 16 and also away from the liquid barrier 20.

Figure 6B:
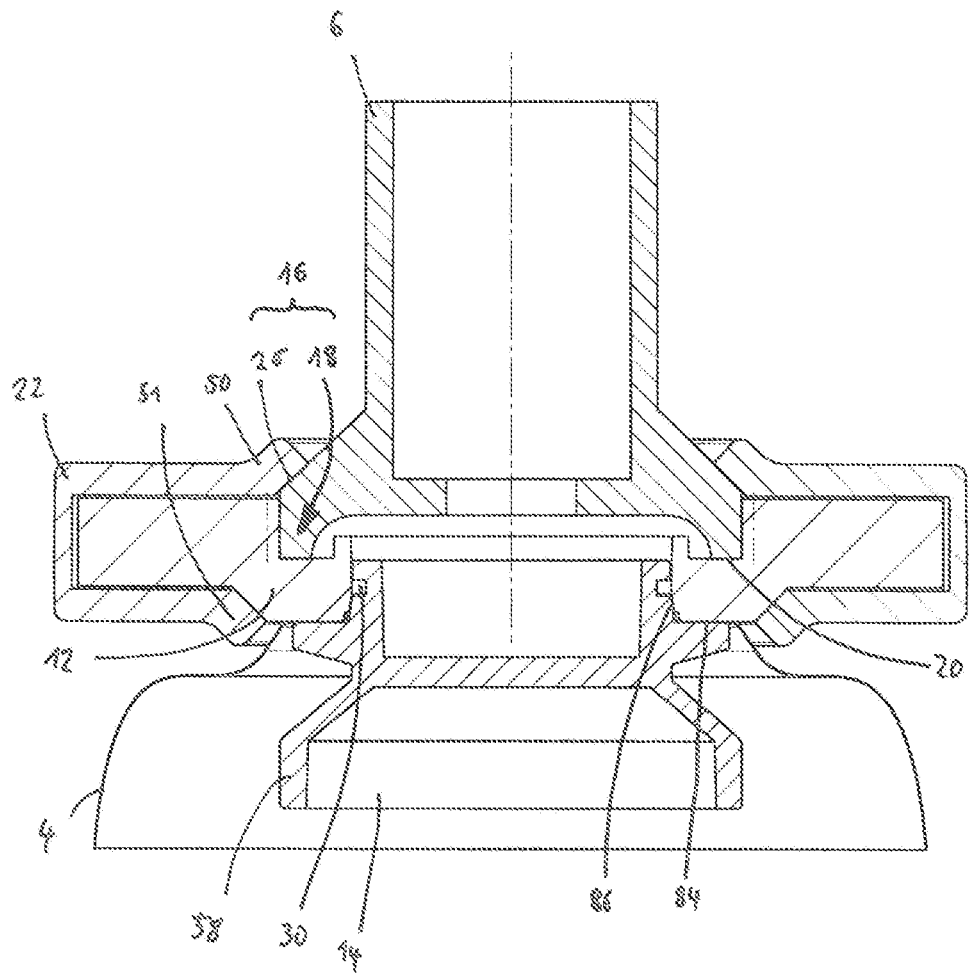
FIG. 6B shows a cross section through line A-A of FIG. 6B.
Figure 6A:
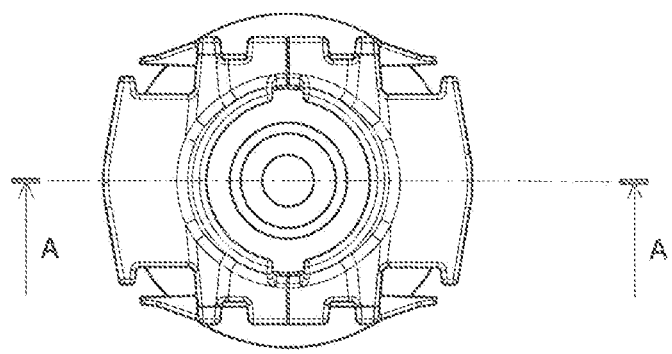
FIG. 6A shows a further embodiment of a coupler according to the disclosure with a drape and an eyepiece cap in a top view.

FIG. 6A shows a further embodiment of the coupler 2 according to the disclosure with a drape 4 (partially shown) and an eyepiece cap 6 (partially shown). FIG. 6B shows a cross section through line A-A of FIG. 6A. This embodiment generally resembles that previously described in the context of FIGS. 3A and 3B. As indicated by FIG. 6B, the liquid barrier 20 may have a planar surface which creates a seal with an opposing surface of the eyepiece cap 6. This surface of the liquid barrier 20 may be integrally formed with base 12. Base 12 may have an opening for holding member 14. The drape 4 may be supported by the coupler 2, connected to base 12 and/or member 14. A part of the drape 4 may be clamped or interlocked or adhesively connected between base 12 and member 14. As indicated by FIG. 6B, the coupler may comprise two fasteners 22 for detachably fastening the eyepiece cap 6 to the coupler 2. FIG. 6B shows the coupler in a closed state. The fasteners 22 may be slid to an open state and vice versa in a direction generally orthogonal to the axis of the eyepiece cap. The fasteners 22 may comprise a fastener-side receiving portion 26.

As indicated by FIG. 6B, in this embodiment, the optically transmissible and liquid impermeable member 14 and the base 12 are connected to form a liquid-tight seal, preferably using a bayonet mount, preferably a snap-fit bayonet mount, e.g., of the type described above. The member 14 may have one or more helical bayonet mount slots 30, which interact with a counterpart at the base 12. A snap-fit cantilever may be in either of the two rotational parts, with a corresponding element on the other rotational part.

Beyond these described features, this embodiment may resemble the embodiment described above, for which reason reference is made to the above descriptions.

Figure 7A:
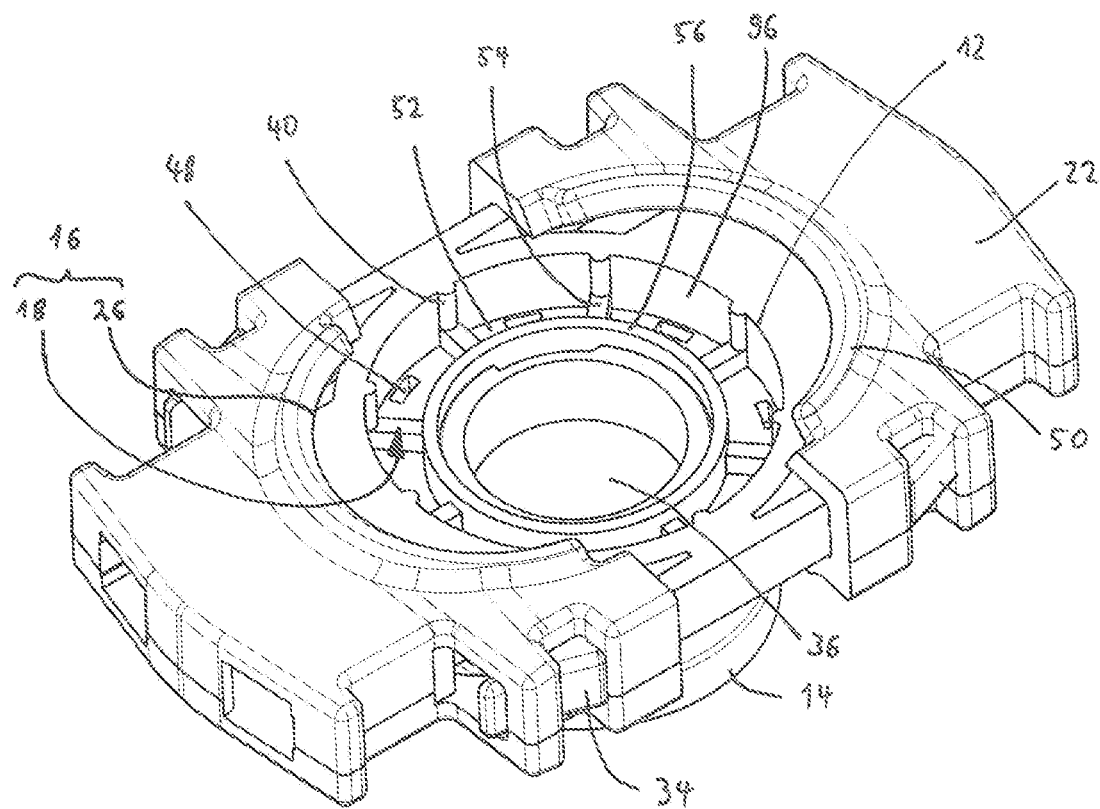
FIG. 7A shows a further embodiment of a coupler according to the disclosure in a perspective view.
Figure 7C:
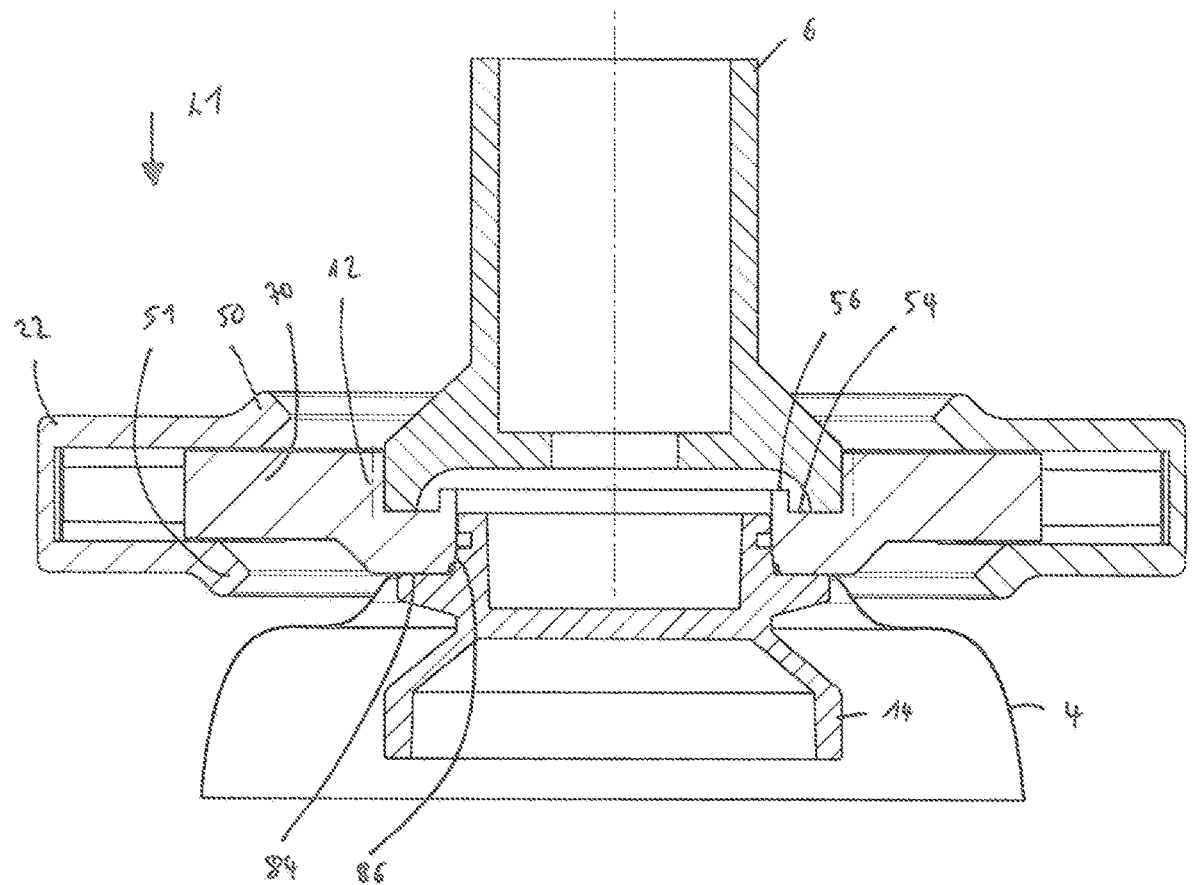
FIG. 7C shows a cross section through line A-A of FIG. 7B.
Figure 7B:
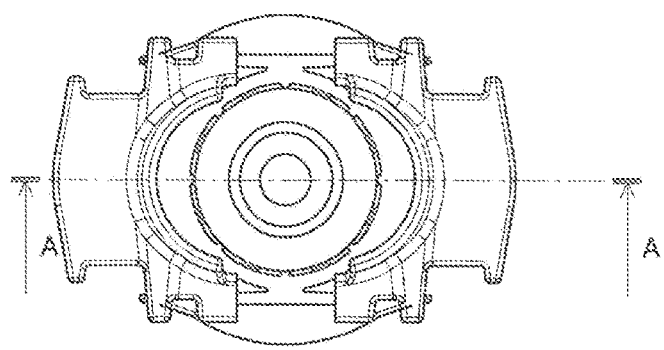
FIG. 7B shows the coupler of FIG. 7A with a drape and an eyepiece cap in an open state in a top view.
Figure 7E:
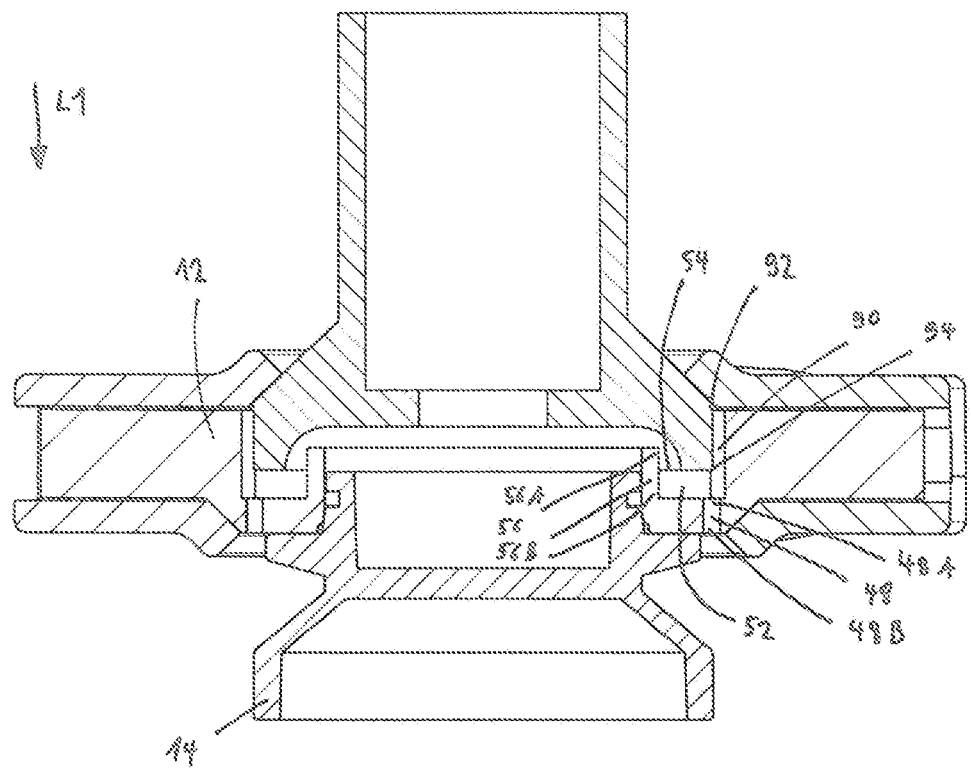
FIG. 7E shows a cross section through line B-B of FIG. 7D.
Figure 7D:
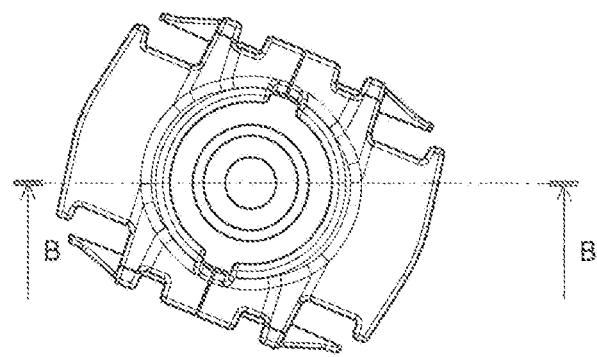
FIG. 7D shows the coupler of FIG. 7A with the drape and the eyepiece cap in a closed state in a top view.
Figure 8:
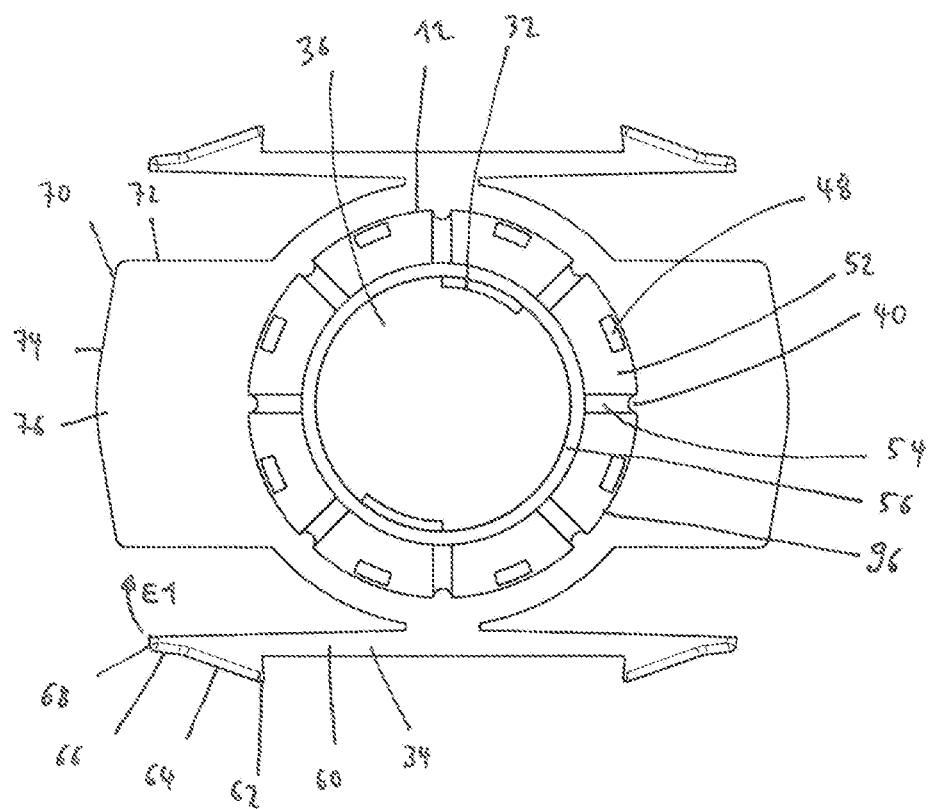
FIG. 8 shows a part of the coupler of FIG. 7A in a top view.

FIG. 7A shows a further embodiment of the coupler 2 according to the disclosure with a drape 4 and an eyepiece cap 6 in a perspective view. FIG. 7B shows the coupler of FIG. 7A with drape and eyepiece cap in an open state in a top view. FIG. 7C is a cross section through line A-A of FIG. 7B. FIG. 7D shows the coupler of FIG. 7A with drape and eyepiece cap in a closed state in a top view. FIG. 7E is a cross section through line B-B of FIG. 7D. FIG. 8 shows a part of coupler of FIG. 7A in a top view. This embodiment has many similarities to that of FIGS. 2-6B, for which reason a person skilled in the art will find much of the above-said applicable to this embodiment and for which reason the description of this embodiment will focus on some deviations.

The liquid barrier of this embodiment may comprise a dam 56 radially outside of the optical path and a liquid collection portion 52 radially outside of the dam. The dam 56 of this embodiment forms at least part of the liquid barrier and may, e.g., comprise two levels in the direction L1, which corresponds to the direction of the axis of the eyepiece cap, and a step between these two levels. The upper of the two levels may be at or near an (upper) dam edge 56A and the lower of the two levels may be at a dam footing 56B. The liquid collection portion 52 may be located so as to surround the dam 56.

This liquid collection portion 52 may comprise, as indicated in FIG. 7A and FIG. 8, several recesses arranged at least partially around the circumference of the dam. Beams 54 and dam 56 and depression wall 96 may delimit the recesses.

Furthermore, the coupler may comprise one or more draining channels 48 for discharging liquid from the liquid barrier. Especially when the direction of gravity is in a generally downward direction, pointing generally parallel to the axis of the eyepiece cap towards member 14 in FIG. 7E, i.e., in the direction L1, but also in other directions, gravity and fluid mechanic effects may keep liquids in the liquid collection portion 52, and may prevent or hinder liquids from passing or "climbing" the dam and entering between eyepiece cap 6 and member 14. As the dam edge 56A is higher than the dam footing 56B when the coupler is positioned in the described orientation, gravitational forces may keep liquids from surpassing the dam edge 56A. The draining channels 48 may contribute to this effect by discharging liquids.

As indicated by FIG. 7C and FIG. 7E, beams 54 may be configured to support the eyepiece cap and keep it in a defined position relative to the dam 56 and the liquid collection portion 52. Multiple beams 54 may be positioned between recesses of liquid collection portion 52. The beams 54 may support the eyepiece cap 6 and keep it distanced from the liquid collection portion 52. Draining channels 48 may lead from recesses of liquid collection portions 52 through the base to the other side of the base. A draining channel 48 may have a discharge entry portion 48A and a discharge exit portion 48B. The discharge entry portion 48A may communicate with the liquid collection portion 52. The discharge exit portion 48B may communicate with the outside, e.g., with an area between the base 12 and the drape 4.

The eyepiece cap 6 may be spaced from the depression wall 96 because it may be held in place by radially inwardly extending projections 40. This may leave a draining space 90. Draining space 90 may extend from an upper portion 92 of the eyepiece cap cylinder portion to a lower portion 94 of the eyepiece cap cylinder portion and/or the liquid collection portion 52 and/or one or more draining channels 48. In other words, the draining space 90 may be formed between the outer cylindrical surface of the eyepiece cap 6 and the depression wall 96 of the depression 38 formed in the base 12.

If, for example, the coupler is held in an orientation where the direction L1 is generally parallel to the direction of gravity and during surgical procedures liquids may follow the direction of gravity and run down the eyepiece cap or enter a space between the eyepiece cap and the coupler or enter draining space 90, the liquids may enter the liquid collection portion 52. Gravity may keep the liquid from surpassing dam edge 56A. The liquid may follow the draining channel 48, entering the discharge entry portion 48A of the draining channel 48 and following the direction of gravity towards the discharge exit portion 48B of the draining channel 48. It may be advantageous to remove liquid from the receiving portion 16 and to clear the liquid collection portion 52. An overflow of the liquid collection portion 52 may result in undesired entry of liquid past the dam 56.

FIG. 8 shows a part of the embodiment shown in FIG. 7A in a top view. This view illustrates recesses of the liquid collection portion 52, delimited by dam 56, beams 54 and depression wall 96. The liquid draining channels 48 communicate with the liquid collection portions 52. Radially inwardly extending protrusions 40 may or may not be arranged proximate the beams 54. Blocks 70 and snap fingers 34 resemble those of the embodiment described with reference to FIG. 5.

The coupler of the embodiment shown in FIG. 7A may comprise a receiving portion 16 for the eyepiece cap 6, wherein the receiving portion 16 comprises a base-side receiving portion 18 configured to receive the eyepiece cap 6 along an insertion path extending exclusively in one direction. Alternatively, the base-side receiving portion 18 may instead not be configured to receive the eyepiece cap 6 along an insertion path extending exclusively in one direction. For example, the base-side receiving portion 18 may instead be configured to receive the eyepiece cap 6 along an insertion path extending in a series of different directions or a multitude of directions. For example, the base-side receiving portion 16 may have an undercut, requiring a multi-directional insertion of the eyepiece cap.

It is within the scope of the disclosure that any embodiment may comprise any of the afore-mentioned features alone or in any combination thereof, unless explicitly otherwise stated.

Figure 9B:
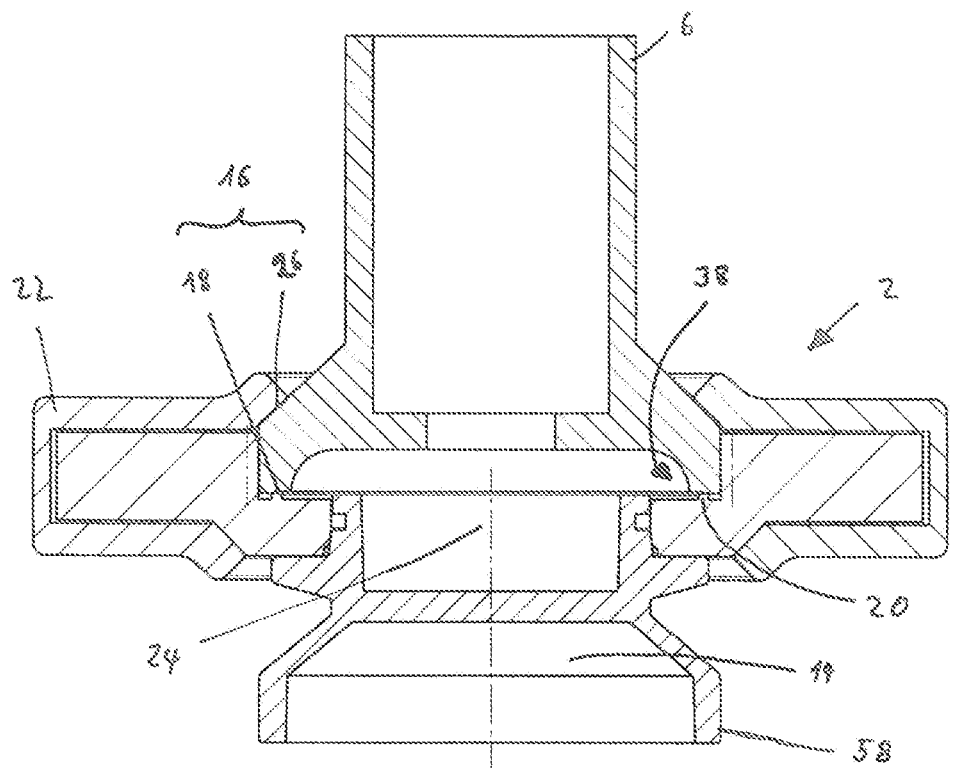
FIG. 9B shows a cross-section through line A-A of FIG. 9B.
Figure 9A:
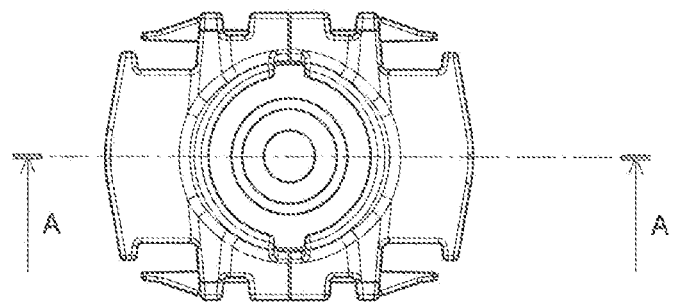
FIG. 9A shows yet another embodiment of a coupler according to the disclosure with a drape and an eyepiece cap in a top view.

FIG. 9A schematically shows another embodiment of the coupler 2 according to the disclosure with the drape 4 and the eyepiece cap 6 in a top view. FIG. 9B shows a cross section through line A-A of FIG. 9A. FIG. 9B shows a coupled state where the coupler 2 is in contact with and attached to the eyepiece cap 6. The drape 4 may be supported by the base 12. It may be attached to the base 12, as indicated in FIG. 9B.

As shown in FIG. 9B, the coupler 2 may receive the eyepiece cap 6. The receiving portion 16 may comprise the base-side receiving portion 18. FIG. 9B shows that the base-side receiving portion 18 may be configured to receive the eyepiece cap 6 along an insertion path extending exclusively in one direction, e.g., in a direction generally parallel to the axis of the eyepiece cap 6. The receiving portion 16 of the coupler 2 may form a generally cylindrical space for the eyepiece cap to be moved along this cylindrical free space.

In the illustrated embodiment, the liquid barrier 20 is provided in the base-side receiving portion 18. As shown in FIG. 9B, the liquid barrier 20 may surround the area of the optical path 24. The liquid barrier 20 may be formed as a sealing lip protruding the bottom of the depression 38. The sealing lip is configured to provide a liquid seal with the eyepiece cap 6 when it is brought in contact with the end surface of the eyepiece cap, as shown in FIG. 9B. The sealing lip may be an integral part of the base. For example, the sealing lip may be made from the same material as the base and may be formed as a thin (flexible) web of said material. Alternatively or additionally, the sealing element may be formed to the base by a multi-component injection molding process, or the like. As an alternative to a sealing lip, sealing protrusions of other shapes are also possible, e.g., sealing elements having other geometric cross-sectional shapes (e.g., rectangular, semi-circular, polygonal). The sealing lip or protrusions of this embodiment may provide a sealing function and form a dam as described above, e.g., in the context of FIGS. 7A-E and 8. In particular, a liquid collection portion 52 may be provided outside of the sealing lip. Furthermore, one or more draining channels 48 may be provided. Such double liquid barrier function can also be foreseen in any other embodiment of the disclosure.

As stated above, the liquid barrier 20 may be elastic and may be of the same material as the base. When in contact, these two surfaces may create a seal. The seal may surround the optical path 24 circumferentially, thereby hindering or preventing liquids from entering between the eyepiece cap 6 and member 14. Alternatively or additionally, the liquid barrier 20 may form a dam which hinders or prevents liquids from entering between eyepiece cap 6 and member 14. As indicated in FIG. 9B, the dam may be part of the base 12 and may be a protrusion or a ridge, circumferentially surrounding member 14.

As shown in FIG. 9B, the coupler 2 may comprise one or two or more fasteners 22 for detachably fastening the eyepiece cap 6 to the coupler 2. The fasteners 22 may have an open state as shown in FIG. 1B and, as indicated in FIG. 9B, a closed state, and may be moved between the two states. These fasteners 22 may comprise a fastener-side receiving portion 26, wherein the receiving portion 16 is cooperatively formed by the base-side receiving portion 18 and the fastener-side receiving portion 26. The fasteners 22 may be configured to apply a compressive force in an axial and/or radial direction with respect to the eyepiece cap in the closed state so as to urge the eyepiece cap 6 into the receiving portion.

Those skilled in the art will recognize that the disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope and spirit of the present disclosure as described in the appended claims.

The invention claimed is:

1. A coupler for detachably coupling an endotherapy eyepiece cap to a camera and supporting a drape for covering the camera, the coupler comprising:
   an optically transmissible and liquid impermeable member configured to be arranged in an optical path between the eyepiece cap and the camera;
   a base configured to hold the optically transmissible and liquid impermeable member in the optical path;
   a receiving portion for the eyepiece cap, wherein the receiving portion comprises a base-side receiving portion configured to receive the eyepiece cap along an insertion path extending exclusively in one direction; and
   a liquid barrier provided in the receiving portion and configured to hinder or prevent liquid from entering between the eyepiece cap and the optically transmissible and liquid impermeable member when the eyepiece cap is coupled to the camera.

2. The coupler according to claim 1, wherein the base has an opening for attachment of the optically transmissible and liquid impermeable member in the optical path.

3. The coupler according to claim 1, wherein the liquid barrier circumferentially surrounds the optical path.

4. The coupler according to claim 1, wherein the liquid barrier comprises a sealing surface configured to contact an opposing sealing surface of the eyepiece cap, thereby creating a seal therebetween.

5. The coupler according to claim 1, wherein the coupler comprises one or more draining channels for discharging liquid from the liquid barrier.

6. The coupler according to claim 1, wherein the receiving portion comprises one or more radially inwardly extending projections configured to position the eyepiece cap or a sealing element, or both, in the receiving portion.

7. The coupler according to claim 1, wherein the receiving portion further comprises a fastener-side receiving portion comprising at least one fastener configured for detachably fastening the eyepiece cap to the coupler.

8. The coupler according to claim 7, wherein the at least one fastener is movably mounted to the base and is configured to be moved to and from an open state and a closed state.

9. The coupler according to claim 8, wherein the at least one fastener is slidable or pivotable, or both, relative to the base to hold the eyepiece cap in place in the closed state, and to release the eyepiece cap in the open state.

10. The coupler according to claim 8, wherein the at least one fastener is configured to apply a compressive force in an axial direction, or radial direction, or both directions, with respect to the eyepiece cap in the closed state so as to urge the eyepiece cap into the receiving portion.

11. The coupler according to claim 8, wherein the at least one fastener and base form a snap-fit mechanism, wherein, in the closed state, the at least one fastener and base are releasably snapped together, and the at least one fastener is biased towards the open state.

12. The coupler according to claim 11, wherein the snap-fit mechanism is a non-permanent cantilever snap-fit mechanism comprising one or more levers, wherein the levers are integral parts of the base.

13. The coupler according to claim 7, wherein the receiving portion is cooperatively formed by the base-side receiving portion and the fastener-side receiving portion.

14. The coupler according to claim 7, wherein the fastener engages contact portions on both sides of the base in an axial direction with respect to the eyepiece cap.

15. The coupler according to claim 7, wherein the receiving portion is formed in a portion of the base and a portion of the at least one fastener.

\* \* \* \* \*